(12) United States Patent
Armani et al.

(10) Patent No.: US 8,310,677 B2
(45) Date of Patent: *Nov. 13, 2012

(54) MICRO-CAVITY GAS AND VAPOR SENSORS AND DETECTION METHODS

(75) Inventors: Andrea M. Armani, Pasadena, CA (US); Tsu-Te J. Su, Boca Raton, FL (US); Richard C. Flagan, Pasadena, CA (US); Scott E. Fraser, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/361,076

(22) Filed: Jan. 30, 2012

(65) Prior Publication Data

US 2012/0120398 A1   May 17, 2012

Related U.S. Application Data

(63) Continuation of application No. 12/243,580, filed on Oct. 1, 2008, now Pat. No. 8,107,081.

(60) Provisional application No. 60/997,141, filed on Oct. 1, 2007, provisional application No. 60/997,142, filed on Oct. 1, 2007, provisional application No. 60/997,143, filed on Oct. 1, 2007.

(51) Int. Cl.
*G01N 21/00* (2006.01)
(52) U.S. Cl. .......................... 356/437; 356/432
(58) Field of Classification Search .......... 356/432–437, 356/442, 480; 372/92–98, 64–67, 108, 39, 372/6; 385/146, 28, 30, 12, 129, 15; 436/172, 436/164; 427/2.13, 2.1, 2.11
See application file for complete search history.

(56) References Cited

U.S. PATENT DOCUMENTS

| | | | |
|---|---|---|---|
| 5,343,490 A | 8/1994 | McCall | |
| 6,259,717 B1 | 7/2001 | Stone et al. | |
| 6,490,039 B2 | 12/2002 | Maleki et al. | |
| 6,657,731 B2 | 12/2003 | Tapalian et al. | |
| 6,741,628 B2 | 5/2004 | Painter et al. | |

(Continued)

FOREIGN PATENT DOCUMENTS

WO    01/40757 A2    6/2001

OTHER PUBLICATIONS

Vollmer, et al."Protein Detection by Optical Shift of a Resonant Microcavity".American Institute of Physics, Applied Physics Letters, vol. 80, No. 21. pp. 4057-4059. May 27, 2002.American Institute of Physics (3 pages).

(Continued)

*Primary Examiner* — Tri T Ton
(74) *Attorney, Agent, or Firm* — Vista IP Law Group LLP; Gary D. Lueck

(57) ABSTRACT

Micro-cavity gas or vapor sensors and gas or vapor detection methods. Optical energy is introduced into a resonant microcavity having a deformable coating such as a polymer. The coating swells or expands when it is exposed to or absorbs a gas or vapor, thereby changing the resonant wavelength of optical energy circulating within the micro-cavity/coating. Expansion or swelling of the coating may be reversible such that it contracts when gas or vapor diffuses from the coating. The coating deformation and/or a change of one or more optical properties of the optical energy circulating within the micro-cavity are used to detect the presence of the gas or vapor or molecules or particulates thereof.

22 Claims, 17 Drawing Sheets

U.S. PATENT DOCUMENTS

| | | |
|---|---|---|
| 7,003,002 B2 | 2/2006 | Vahala et al. |
| 7,012,696 B2 | 3/2006 | Orr et al. |
| 7,545,843 B2 | 6/2009 | Armani et al. |
| 2002/0018611 A1 | 2/2002 | Maleki et al. |
| 2004/0115824 A1 | 6/2004 | Ponce et al. |
| 2005/0163185 A1 | 7/2005 | Vahala et al. |
| 2005/0169331 A1 | 8/2005 | Vahala et al. |
| 2006/0170931 A1 | 8/2006 | Guo et al. |
| 2007/0153284 A1 | 7/2007 | Glazier et al. |
| 2007/0269901 A1 | 11/2007 | Armani et al. |
| 2009/0097031 A1 | 4/2009 | Armani et al. |
| 2009/0214755 A1 | 8/2009 | Armani et al. |
| 2009/0310902 A1 | 12/2009 | Smith et al. |

OTHER PUBLICATIONS

D. Armani et al."Ultra-high-Q toroid microcavity on a chip". Letters to Nature. Department of Applied Physics, California Institute of Technology, Pasadena CA. 2003 Nature Publishing Group. Nature, vol. 421, Feb. 27, 2003. pp. 925-928. (5 pages).

J. Niehusmann et al."Ultrahigh-quality-factor silicon-on insulator microring resonator". Optics Letters vol. 29,No. 24. pp. 2861-2863, Optical Society of America, 2004. Dec. 15, 2004. (4 pages).

J. Yao, et al "Silicon Microtoroidal Resonators with Integrated MEMS Tunable Laser". IEEE Journal of selected topics in Quantum Electronics, vol. 13, No. 2. Mar./Apr. 2007. p. 202-208.(2). (15 pages).

Prosecution History Papers U.S. Appl. No. 10/678,354, filed Oct. 2, 2003. (Notice of Allowance Feb. 27, 2009 (7pages); Alppeal Brief Nov. 25, 2008 ( 128 pgs); Advisory Action Nov. 5, 2008 (6 pages; Amendment of Aug. 9, 2008 (1pg);Applicant Summary of Interview May 9, 2008 (31 pgs); Examiner Interview Summary Record Mar. 7, 2008 (2pgs); Amendment Jul. 30, 2007 (1 pg); Applicant Summary of Interview May 14, 2007 (2pgs); Non-final rejection of Apr. 30, 2007(10pgs).

Prosecution History Papers in U.S. Appl. No. 11/733,480, filed Apr. 10, 2007 (Non-Final Rejection Jul. 16, 2009 (15 pgs); Amendment of May 8, 2009 (1pg); Final Rejection Jan. 8, 2009 (22pgs); Amendment Oct. 1, 2008 (1pg); Non-Final Rejection of Jul. 10, 2008 (18pgs); Amendment Apr. 10, 2008(1pg); Non-Final Rejection Dec. 10, 2007 (12pgs)).

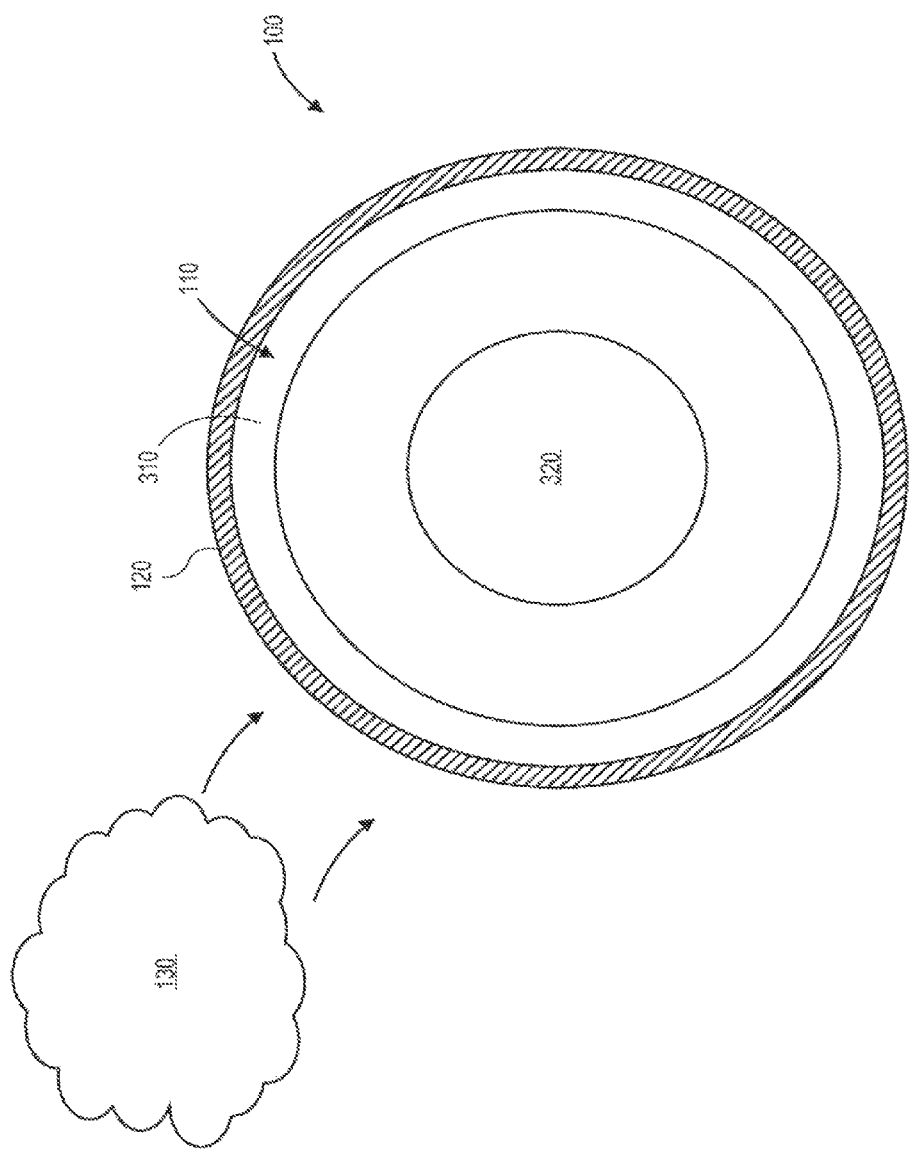

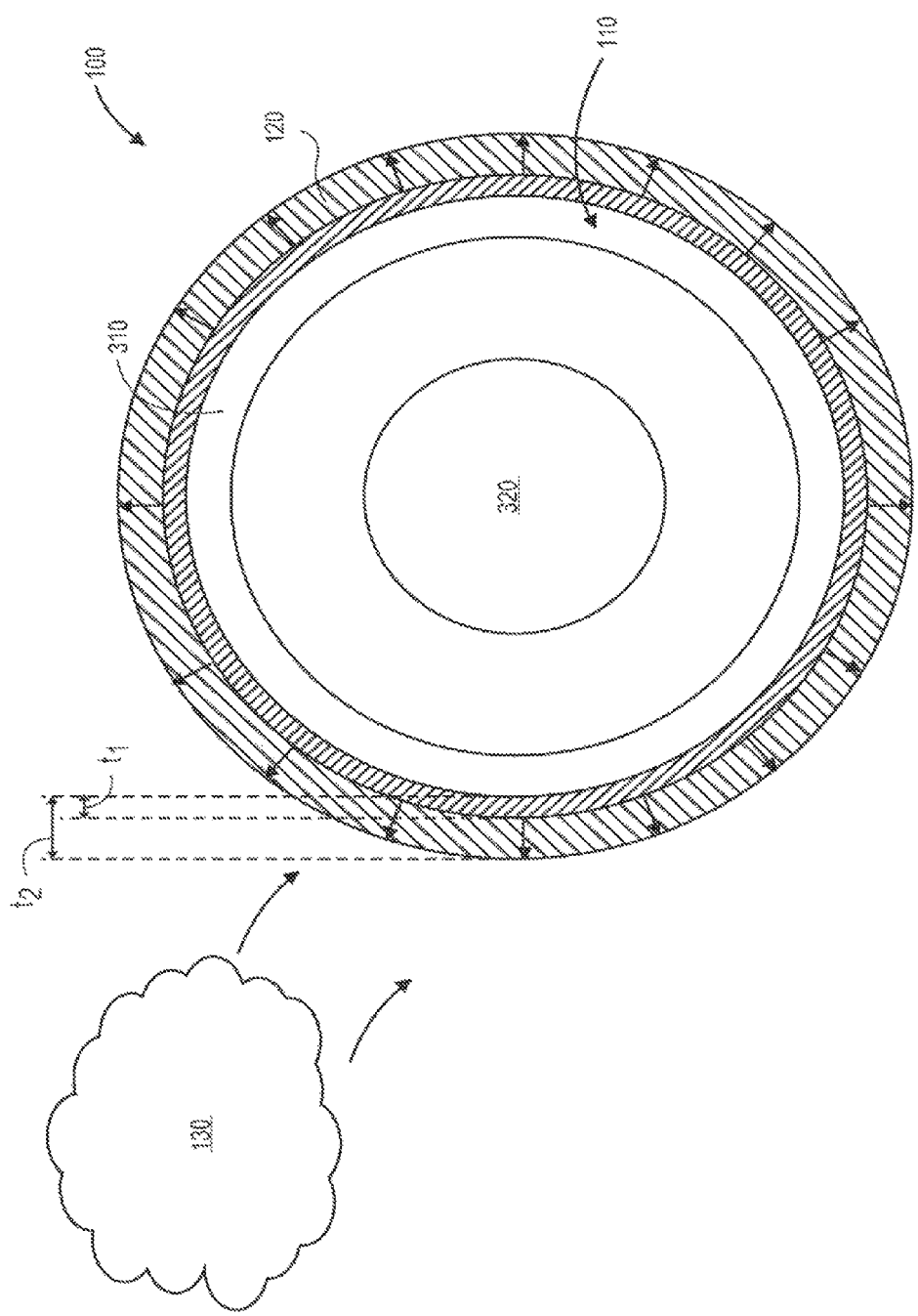

MICRO-CAVITY GAS AND VAPOR SENSORS AND DETECTION METHODS

CROSS REFERENCE TO RELATED APPLICATIONS

This application is a continuation of co-pending U.S. application Ser. No. 12/243,580, filed Oct. 1, 2008, which claims the benefit under 35 U.S.C. §119 of U.S. Provisional Application Ser. Nos. 60/997,141; 60/997,142 and 60/997,143, all of which were filed on Oct. 1, 2007, the contents of all of which are incorporated herein by reference as though set forth in full.

This application may also be related to the following applications, the contents of which are also incorporated herein by reference as though set forth in full: U.S. application Ser. No. 11/733,480 (Publication No. 2007/0269901) and U.S. application Ser. No. 10/678,354 (Publication No. 2004/0179573).

STATEMENT REGARDING FEDERALLY SPONSORED RESEARCH

Not Applicable.

FIELD OF INVENTION

The present invention relates to micro-cavity gas or vapor sensors and associated detection methods.

BACKGROUND

Various known sensor devices and methods have been utilized to detect different types of target molecules or particulates. Certain sensors involve detection or measurement of biological elements utilizing antibody-antigen interactions. With these types of biological sensors, a surface or sensor can be labeled such that highly specific responses to molecules of interest can be generated. While such sensors may have high specificity, they may also have a number of limitations including inadequate sensitivity and limited applications, particularly in the context of gas or vapor detection. For example, such biological sensors may be suitable for detecting certain gas or vapor molecules that have synthetically matched antibodies (such as Trinitrotoluene or "TNT"), but most gas or vapor molecules do not involve matched antibodies and the same degree of surface specificity.

Emission and absorption spectroscopic techniques may appear to be suitable methods for use in gas or vapor detection since they provide a "chemical fingerprint" of individual molecules in a mixture. However, such systems and methods have limited sensitivities for detection of a number of gas or vapor molecules and particulates of interest.

Other known sensors and detection methods also involve limited specificity, sensitivities and/or limited applications such that they are not suitable or are not satisfactory for various gas or vapor sensing applications. In addition to these limitations, response times of sensors suitable for use in gas or vapor environments are often slow, particularly following exposure to high concentrations of a gas or vapor.

SUMMARY

One embodiment is directed to a method for detecting a gas or vapor that comprises introducing optical energy into a micro-cavity having a coating or film and detecting the gas or vapor based on deformation of the coating. Deformation of the coating results from the coating absorbing the gas or vapor.

Another embodiment is directed to a method for detecting a gas or vapor that comprises introducing optical energy into a micro-cavity having a polymer coating and detecting the gas or vapor based on a resonant wavelength shift of the optical energy. The resonant wavelength shift is caused by deformation of the polymer coating, which results from absorption of the gas or vapor by the polymer coating.

A further embodiment is directed to a method for detecting a gas or vapor that comprises introducing optical energy into an ultra-high Q optical micro-cavity having a polymer coating and detecting the gas or vapor based on deformation of the polymer coating, which results from absorption of the gas or vapor by the polymer coating.

Yet another alternative embodiment is directed to a sensor for detecting gas or vapor. The sensor comprises an optical micro-cavity and a coating on an outer surface of the optical micro-cavity. The coating has material properties or is structured or configured to deform as a result of absorbing the gas or vapor to alter optical energy resonating within the optical micro-cavity to indicate the presence of the gas or vapor.

Another alternative embodiment is directed to a sensor for detecting a gas or vapor that comprises an optical micro-cavity and a polymer coating or film on an outer surface of the micro-cavity. The polymer coating has material properties or is structured or configured to deform as a result of absorbing the gas or vapor and to shift a resonant wavelength of optical energy resonating within the micro-cavity to indicate the presence of the gas or vapor.

An additional embodiment is directed to a sensor for detecting a gas or vapor that comprises an ultra-high Q micro-cavity and a polymer coating on an outer surface of the micro-cavity. The polymer coating has material properties or is structured or configured to deform as a result of absorbing the gas or vapor and to alter optical energy resonating within the micro-cavity to indicate the presence of the gas or vapor.

In one or more embodiments, the coating, which may be a polymer such as Polymethyl methacrylate (PMMA), polyethyleneimine, Nafion®, fluorosciloxane or polyp-xylylene), or another deformable coating, may expand or swell or may contract as a result of absorbing the gas or vapor. Expansion or contraction of the micro-cavity may also be reversible. Thus, if the coating expands as a result of absorption of the gas or vapor, the coating may contract as a result of diffusion of the gas or vapor from the coating. Similarly, if the coating contracts as a result of absorption of the gas or vapor, then it may expand as a result of diffusion of the gas or vapor from the coating. These changes are used to detect a gas or vapor while optical energy resonates within the micro-cavity. A sensor may also be re-usable for subsequent detection.

In one or more embodiments, physical changes of the deformable coating and/or changes of optical energy resonating within a coated micro-cavity may be used to detect various types of target molecules or particulates in a gaseous environment, gases or vapors including, but not limited to, nitrogen dioxide ($NO_2$), ammonia ($NH_3$), a chlorinated hydrocarbon, an aromatic hydrocarbon, an aliphatic hydrocarbon, an acetate, an alcohol, 1,2-dichloroethane, bromochloromethane, trichloromethane, dichloromethane or tetrachloromethane and other gases or vapors.

In one or more embodiments, a gas or vapor is detected based on a change of one or more of a dimension (e.g., diameter, height or thickness) of the coating, a dimension of a combination of the micro-cavity and the coating, and an optical property (e.g., resonant wavelength) of the optical energy resonating within the micro-cavity and/or coating. For example, expansion or swelling of the coating may cause a red shift of the resonant wavelength of the optical energy resonating in the micro-cavity, whereas contraction of the coating may cause a blue shift of the resonant wavelength of the optical energy.

In one or more embodiments, a gas or vapor sensor includes a planar micro-cavity. The planar micro-cavity may be in the form of a toroid, a disk, or a ring. Other embodiments of a gas or vapor sensor include a non-planar micro-cavity such as a micro-sphere.

The optical micro-cavity may be made of various materials including silica. Embodiments may be implemented using a single coated micro-cavity or array of coated micro-cavities. Micro-cavities in an array may have the same or different diameters, be made of the same or different materials, and have the same or different coatings to provide for different resonant wavelengths and different responses to different gases and vapors. Sensors may be implemented using micro-cavities having Q values that are greater than 1,000 and micro-cavities having substantially higher Q values, e.g., ultra-high Q values greater than $10^6$. Embodiments may be utilized to detect various types of gases and vapors and may be used in various applications including but not limited to environmental monitoring, explosives detection, toxicology and medical diagnostics and embodiments may be used to detect unlabeled molecules in gas or vapor.

In one or more embodiments, the micro-cavity may be supported by a substrate. The micro-cavity and the substrate are configured such that an outer edge of the micro-cavity extends outwardly beyond a top of the substrate. For example, the substrate may extend upwardly and taper such that the micro-cavity extends beyond the outer edge of the top of the substrate.

BRIEF DESCRIPTION OF THE DRAWINGS

The foregoing and other aspects of embodiments will best be appreciated with reference to the detailed description of illustrated embodiments in conjunction with the accompanying drawings, wherein:

FIGS. 11A-D are more detailed top view illustrations of a gas or vapor sensor constructed according to one embodiment and including a toroid-shaped micro-cavity and a deformable coating at various detection stages of detecting a gas or vapor, FIG. 11A illustrating a gas or vapor sensor and dimensions thereof, FIG. 11B illustrating the gas or vapor sensor being exposed to or placed within a gas or vapor environment; FIG. 11C illustrating the deformable coating absorbing the gas or vapor and expanding or swelling, and FIG. 11D illustrates diffusion of gas or vapor from the coating thereby resulting in contraction of the coating, e.g., to a thickness or size before being exposed to the gas or vapor;

DETAILED DESCRIPTION OF ILLUSTRATED EMBODIMENTS

Embodiments of the invention are related to a sensor and arrays of sensors for detecting gas or vapor molecules and aerosols, airborne particulates or collections of gas or vapor molecules (generally referred to as "gas or vapor"). Gas or vapor sensor embodiments include an optical or resonant micro-cavity (generally referred to as "micro-cavity") and a deformable coating or film (generally referred to as a "coating" or "deformable coating") that is applied to at least a portion of an outer surface of the micro-cavity. The micro-cavity and the deformable coating collectively form a hybrid gas or vapor sensor that is used to detect the presence of certain target gases or vapors. During use, optical energy is introduced into the coated micro-cavity and resonates within the micro-cavity and/or the deformable coating, e.g., along an outer portion of the micro-cavity and into the deformable coating. The coating changes shape and/or size as a result of absorbing the gas or vapor. These physical changes and/or the resulting changes of a property of the optical energy resonating within the micro-cavity and/or deformable coating are used to detect the presence of the gas or vapor.

Thus, embodiments provide a gas or vapor sensor that functions in a different manner compared to other resonator sensing devices that rely on a thermo-optic effects or antibody-antigen interactions. Instead, embodiments employ detection methods that are based on deformation of a coating on the micro-cavity. In this manner, embodiments are able to provide detection capabilities in gases or vapors (as opposed to liquid or aqueous environments) and high sensitivities and specificity to discriminate between different gases or vapors while also providing fast response times as a result of the fast deformation of the deformable coating when the coating is exposed to or placed within a gas or vapor environment.

Multiple gas or vapor sensors may form an array of gas or vapor sensors. Sensors in an array may have gas or vapor sensors of different diameters, materials, shapes, Q values, and/or deformable coatings to provide different or customized detection capabilities. Sensors of an array can have different sizes may have different resonant wavelengths to allow for high throughput detection of multiple gases or vapors. Sensors and arrays thereof can also be configured for integration on a chip.

Embodiments can be used in various gas/vapor detection applications including, for example, explosives detection, environmental monitoring, chemical detection, toxicology, medical diagnostics and other applications and may be included in gas sampling and concentration systems including, for example, cryogenic, sorbent trapping, polyurethane foam, activated carbon, molecule sieve, semi-permeable membrane sampling or concentration systems. Embodiments of the invention are described in further detail with reference to FIGS. 1A-14.

Figure 1A:
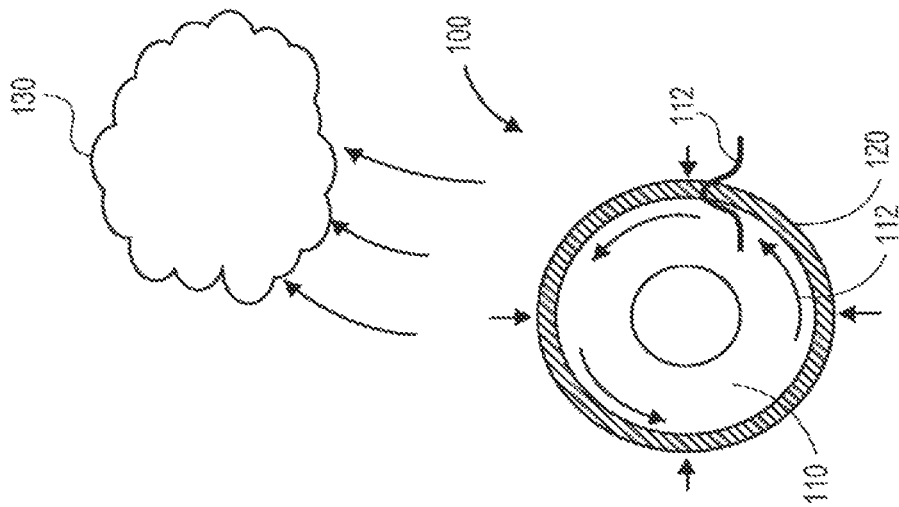
FIGS. 1A-C illustrate a gas or vapor sensor constructed according to one embodiment and having a deformable coating or film on an outer surface of a resonant micro-cavity and detection of a gas or vapor, FIG. 1A illustrating a coated micro-cavity that is not exposed to or placed within a gas or vapor environment, FIG. 1B illustrating the micro-cavity exposed to or placed within a gas or vapor environment and the coating absorbing the gas or vapor and deforming or changing shape and/or size, and FIG. 1C illustrating the gas or vapor diffusing from the coating and reversibility of coating deformation.

Referring to FIG. 1A, a gas or vapor sensor 100 constructed according to one embodiment comprises an optical or resonant micro-cavity or micro-resonator 110 (generally referred to as "micro-cavity" 110) and a deformable material, coating or film 120 (generally referred to as "coating" or "deformable coating" 120) on at least a portion of, or covering, an outer surface of the micro-cavity 110. FIG. 1A is representative of a top view of a micro-cavity 110 having a circular cross-sectional shape to provide a circular optical path for optical energy 112 that resonates or circulates within the micro-cavity 110. For ease of illustration, the optical energy 112 is shown as resonating along an inner surface of the micro-cavity 110, but it should be understood that the optical energy 112 may resonate within different portions of the micro-cavity 110 and within the coating 120. Further, optical energy 112 may evanesce beyond an outer edge of the coating 120, e.g., for purposes of coupling to another system component such as a waveguide, sensor or detector.

Micro-cavities 110 of various shapes, sizes and configurations may be utilized in sensor 100 embodiments and may be partially or completely coated with the deformable coating 120. The micro-cavity 110 may be made of various materials, and different combinations of micro-cavity 110/coating 120 materials may be utilized. In certain embodiments, the micro-cavity 110 is made of a semiconductor material. In other embodiments, the micro-cavity 110 is made of an insulator material. For example, in certain embodiments, the micro-cavity 110 is made of silicon, silica, glass, silicon nitride, a polymer such as a composite polymer and combinations of materials such as polymer coated silica and other suitable resonant micro-cavity 110 materials and combinations thereof.

In certain embodiments, the micro-cavity 110 has a planar shape and be in the form of a disk, ring or toroid-shaped micro-cavity. Other micro-cavity 110 shapes that may be used in sensor 100 embodiments include pillar and spherical shaped micro-cavities. One or more or all of the micro-cavity 110 material, shape and surface qualities affect the Q value of the micro-cavity 110, which may, for example, be about a 1,000 and significantly higher, e.g., $10^6$ or higher. The micro-cavity 110 material, size, shape, surface qualities and/or method of fabrication can be configured and adjusted to provide sufficiently high Q values for providing sufficient sensitivity.

In certain embodiments, the deformable coating 120 is a polymer material. Polymers that are suitable for use in sensor 100 embodiments include, but are not limited to, polymethyl methacrylate (PMMA), polyethyleneimine, Nafion®, fluorosiloxane and polyp-xylylene). In one embodiment, the micro-cavity 110 is silica and the deformable coating 120 is a polymer such as PMMA. For ease of explanation, gas or vapor sensor 100 embodiments are described in further detail with reference to a silica micro-cavity 110 having a PMMA coating 120, but it should be understood that gas or vapor sensors 100 may be implemented using various micro-cavity 110 and coating 120 materials and combinations thereof. Accordingly, the examples provided above and described in further detail below are not intended to limit the scope of embodiments.

Figure 1B:
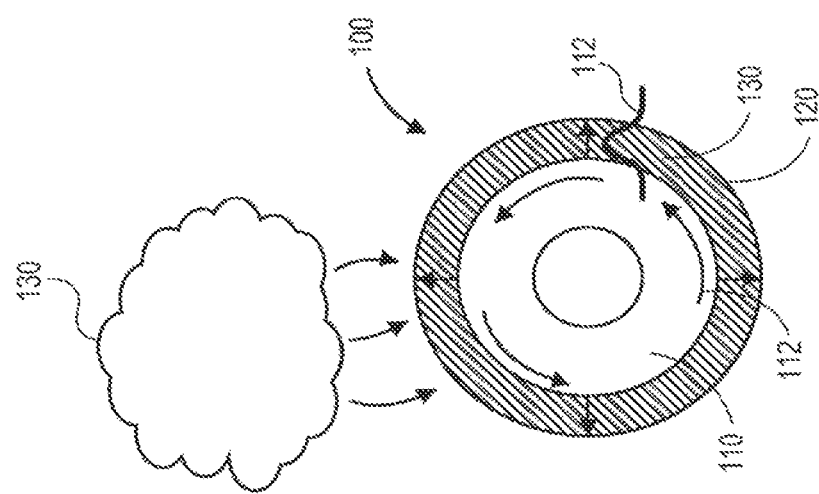

Referring to FIG. 1B, material properties of the coating 120 are such that the coating absorbs gas or vapor 130 when the sensor 100 is exposed to or placed within certain gases or vapors 130. According to one embodiment, as generally illustrated in FIG. 1B, the coating 120 expands or swells (represented by outwardly directed radial arrows) when the coating 120 absorbs the gas or vapor 130. As a result, the area in which the optical energy 112 also expands since the optical energy 112 resonates within the micro-cavity 110 and the expanded coating 120. The extent and/or rate of swelling of the coating 120 may depend on, for example, one or more or all of the type or material properties of the coating 120 (e.g., molecular weight), the thickness of coating 120 and the concentration of the vapor or gas 130. These factors also contribute to the temporal response time of the sensor 100, which may, for example, be between about 1 microsecond and about 1 minute.

The micro-cavity 110 may also increase in size by a small or negligible degree, but since the swelling or deformation of the coating 120 is substantially larger and dominant relative to any change in size of the micro-cavity 110, gas or vapor detection is based on deformation of the coating 120 and associated effects of such deformation upon the optical energy 112 resonating within the micro-cavity 110/coating 120.

In certain embodiments, depending on the type of micro-cavity 110, the micro-cavity 110 has a width or outer diameter of about 30 micrometers to about 3 millimeters, e.g., about 30 micrometers to about 200 micrometers, e.g., about 100 micrometers, and may be made of, for example, a semiconductor or insulator material. For example, a planar micro-cavity 110 may be made of silicon or silica and have a diameter of about 5 micrometers to about 1 millimeter, and a spherical micro-cavity may be made of silica and have a diameter of about 100 micrometers to about 3 millimeters. In certain embodiments, the coating 120 has a thickness of about 10 nanometers to about 2 micrometers, e.g., about 0.5 micrometer. The coating 120 may expand or swell by different degrees and at different rates depending on, for example, one or more or all of the type or material properties of the coating 120 (e.g., molecular weight of the coating 120), the thickness of coating 120, and the concentration of the vapor or gas 130. These factors also contribute to the temporal response time of the sensor 100, i.e., how fast the coating 120 deforms or changes in response to absorption of the gas or vapor 130 to indicate presence of the gas or vapor 130.

According to one embodiment, absorption of the gas or vapor 130 causes the coating 120 to expand or swell (indicated by outwardly directed arrows in FIG. 1B) by about 1% to about 50%, e.g., by about 25%, relative to its original size (FIG. 1A). Swelling of the coating 120 may occur at a rate of about 1 micrometer per second. For example, a coating 120 having a thickness of about 1 micrometer may expand to a thickness of about 1.1 micrometers in about 0.1 second as a result of absorption of the gas or vapor 130 by the coating 120. Thus, the outer or major diameter of the combination of the micro-cavity 110 and the coating 120 may vary by about 0.2 micrometer between initial (FIG. 1A) and expanded or swelled (FIG. 1B) states. The height of the combination of the micro-cavity 110 and the coating 120 may also vary as a result of the expansion.

Figure 1C:
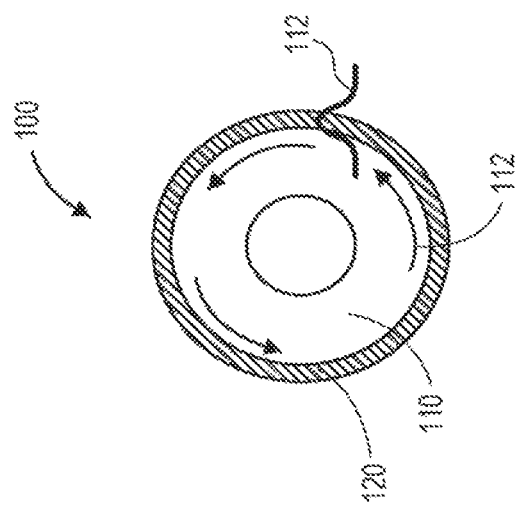

Referring to FIG. 1C, according to one embodiment, the gas or vapor sensor 100 is reversible. In these embodiments, the coating 120 contracts or shrinks (represented by inwardly directed arrows in FIG. 1C) when absorbed gas or vapor 130 diffuses out of the coating 120, thus reducing the area in which the optical energy 112 resonates. In this manner, the sensor 100 can be re-used in point measurements, for example, to track transient changes in vapor concentration.

In other embodiments, material properties of the coating 120 are such that absorption of the gas or vapor 130 by the coating 120 results in contraction of the coating 120, and if the sensor 100 is reversible, diffusion of the gas or vapor 130 from the coating 120 results in expansion or swelling of the coating 120. Detection of the gas or vapor 130 can be performed in a similar manner as described above except that detection is based on contraction of the coating 120 rather than expansion or swelling of the coating 120. For ease of explanation, reference is made to a coating 120 that expands or swells as a result of absorption of the gas or vapor 130.

Figure 2:
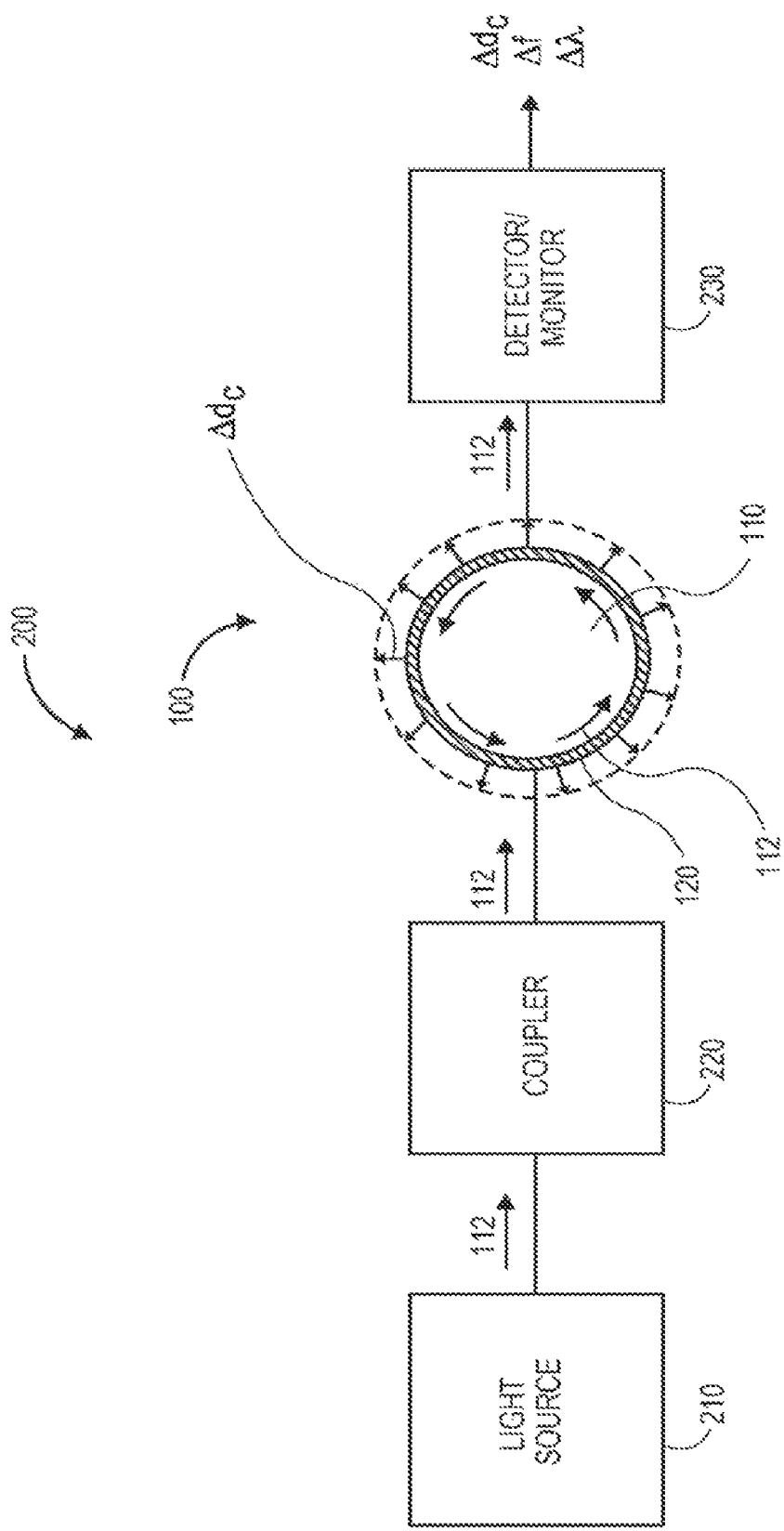
FIG. 2 is a block diagram of a gas or vapor sensor system constructed according to one embodiment that includes a gas or vapor sensor having a resonant micro-cavity and a deformable coating.

Referring to FIG. 2, a micro-cavity 110 having a deformable coating 120 as described with reference to FIGS. 1A-C may be part of a detection system 200 (generally illustrated in FIG. 2) that is used to detect the presence of target gaseous or vapor molecules and airborne particulates or aerosols 130. As generally illustrated in FIG. 2, the detection system 200 includes a light source 210, such as a laser or other suitable source that emits light or optical energy 112, a coupler or waveguide 220 to introduce the light or optical energy 112 into the micro-cavity 110, and a detector or sensor 230 (generally referred to as detector 230). The detector 230 is arranged and utilized to sense or determine the presence of a gas or vapor 130 based on a physical change of the deformable coating 120 and/or a change of one or more optical properties of the optical energy 112 resonating within the micro-cavity 110 and/or coating 120 (e.g., by evanescent coupling). The detector 230 may also be operably coupled to a monitor or display (not illustrated in FIG. 2) such that data or results can be displayed to a user. The data or results generated by the detector 230 may also be provided to another system component, controller or computer that initiates an appropriate action in response to detection of a gas or vapor 130.

According to one embodiment, the detector 230 determines the presence of a target gas or vapor 130 as a result of the increase or decrease in size of the coating 120, e.g., based on a change of dimension such as the width and/or height of the coating 120. According to another embodiment, the detector 230 determines the presence of a target gas or vapor 130 as a result of the increase or decrease in size of the combination of the micro-cavity 110 and the coating 120. For these purposes, the detector 230 can be configured and positioned to measure changes in dimensions using, for example, a microscope, other viewing, image capture or measurement equipment.

According to another embodiment, the detector 230 is configured to determine the presence of a target gas or vapor 230 as a result of a change of one or more optical properties of optical energy 112 that resonates within the micro-cavity 110 and/or coating 120. For this purpose, in one embodiment, the detector is positioned or arranged to detect a portion of optical energy 112 that evanesces beyond the outer edge of the coating 120. In another embodiment, a combination of physical attributes of the coating 120 and optical properties of the optical energy 112 are utilized to detect the gas or vapor 130.

According to one embodiment, the detector 230 is configured to determine the change of the wavelength of the optical energy 112 resonating within the micro-cavity 110/coating 120 by comparing the wavelength of optical energy 112 before exposure to the gas or vapor 230 (FIG. 1A) and the wavelength of optical energy 112 after exposure to and absorption of the gas or vapor 230 and resulting deformation of the coating 120 (FIG. 1B). The wavelength of the optical energy 112 changes as a result of one or more of the refractive index, diameter, and optical losses of the micro-cavity 110/coating 120 caused by deformation of the coating 120. In this manner, the changes in the environment or the gas or vapor 130 to which the sensor 100 is exposed are directly reflected in the resonant wavelength of the optical energy 112 and/or Q factor of the micro-cavity 110/coating 120.

For example, when the coating 120 expands due to absorption of the gas or vapor 130, the expansion causes a red shift in the wavelength (longer wavelength) of optical energy 112 that resonates within the micro-cavity 110. Further, in embodiments in which this effect is reversible, as gas or vapor 130 diffuses out of the coating 120, the coating 120 contracts, thereby causing a blue shift of the wavelength (shorter wavelength) of optical energy 112 resonating within the micro-cavity 110/coating 120. For example, the wavelength of optical energy 112 resonating within a micro-cavity 110/coating 120 prior to exposure to a gas or vapor 130 may be 633.00 nanometers, and the wavelength of the optical energy 112 may increase to about 633.05 nanometers as a result of the coating 120 expanding or swelling when absorbing the gas or vapor 130. These optical changes can be sensed by the detector 230 to determine the presence of a gas or vapor 130 associated with these changes.

Embodiments of gas or vapor sensors 100 may be implemented using various types, numbers and arrangements of micro-cavities 110 that are fabricated with different systems and methods. For example, micro-cavities 110 can be fabricated using known lithography patterning methods and known resonant wavelengths and orientation.

Micro-cavities 110 can also be polymer micro-cavities that are fabricated using replica molding techniques, e.g., as described in U.S. Pat. No. 7,236,664, the contents of which are incorporated herein by reference as though set forth in full. Replica molding techniques are used to fabricate polymer micro-resonators by applying a liquid polymer material to a micro-resonator master that includes at least one micro-resonator, such as a disk or toroid micro-resonator. The liquid molding material is cured or set to form a mold that is derived from the master, and a replica of the master micro-resonator is cast using the mold and separated from the mold. For example, in certain embodiments, the material of the micro-cavity 110 is a composite polymer, and these micro-cavities 110 may be coated with a deformable coating or film 120, which is another type of polymer, using known techniques to form a gas or vapor sensor 100.

In one embodiment, the micro-cavity 110 is a toroid-shaped micro-cavity. Replica molding can be utilized to fabricate toroid-shaped micro-cavities, as described in U.S. Pat. No. 7,236,664, the contents of which were previously incorporated herein by reference. Another method of fabrication of such micro-cavities 110 is described with reference to FIGS. 3-5C and described in further detail in U.S. application Ser. No. 10/678,354 (Publication No. 2004/0179573), the contents of which were also previously incorporated herein by reference. Embodiments of a gas or vapor sensor 100 including a toroid-shaped micro-cavity and a deformable coating 120 are described with reference to FIGS. 6A-12.

Figure 3:
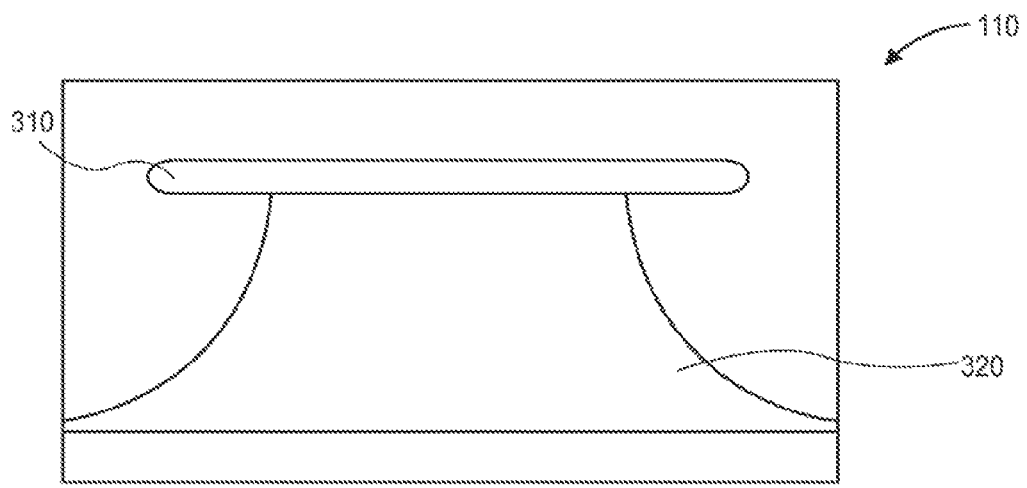
FIG. 3 is a side view of a toroid-shaped micro-cavity of a gas or vapor sensor constructed according to one embodiment.

Referring to FIG. 3, which is a scanning electron micrograph, one embodiment of a gas or vapor sensor 100 comprises a micro-cavity 110 in the form of a toroid-shaped micro-cavity 310 to which a deformable coating 120 is applied. One suitable toroid-shaped micro-cavity 310 is made of silica and is supported by a silicon substrate 320. The radius of a toroid-shaped micro-cavity 310 may vary and may, for example, be about 15 to 100 micrometers, e.g., about 45 micrometers, and may have high Q values and ultra-high Q values (greater than $10^6$). In the illustrated example, the substrate 320 is tapered such that the micro-cavity 310 extends outwardly beyond the outer edge or top of the substrate 320. A polymer coating 120 (not illustrated in FIG. 3) may be applied to an outer surface of the toroid-shaped micro-cavity 310.

Figure 4:
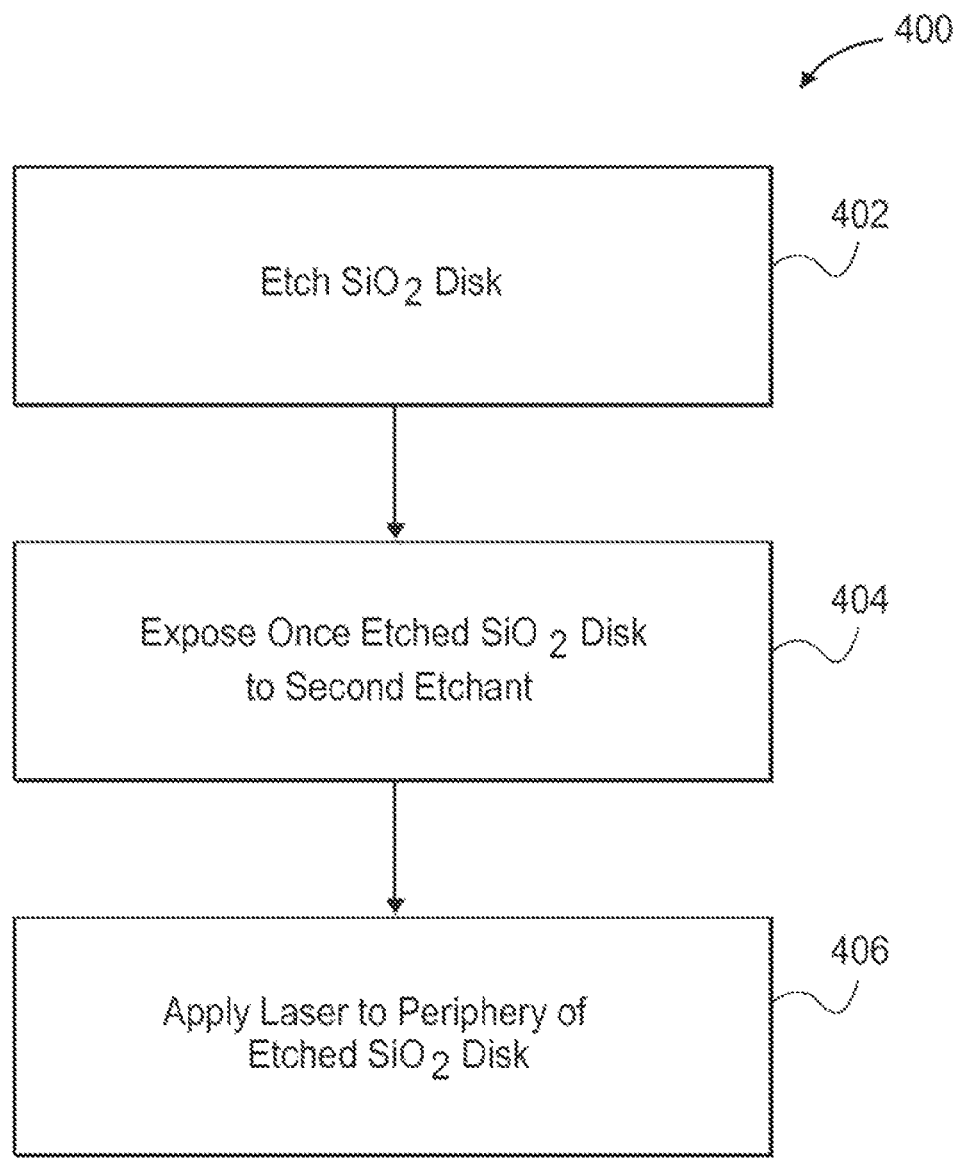
FIG. 4 is a flow diagram illustrating a method of manufacturing a toroid-shaped micro-cavity as shown in FIG. 3.
Figure 5A:
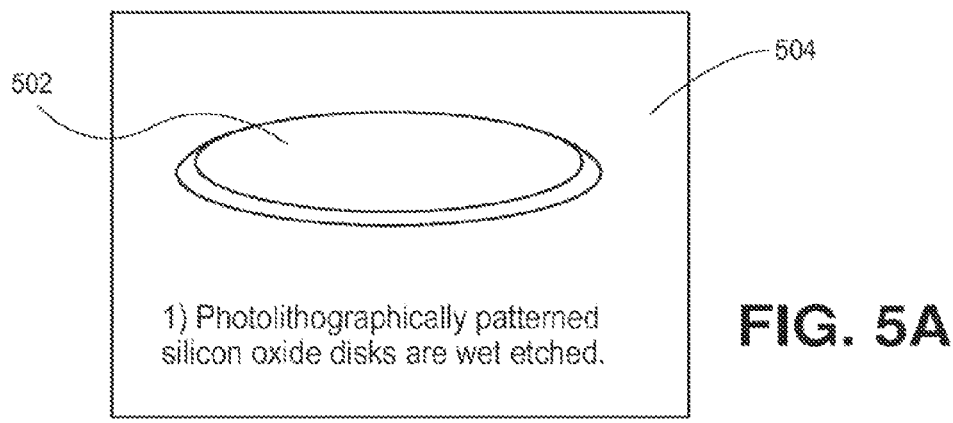
FIGS. 5A-C further illustrate fabrication stages of the method shown in FIG. 4.
Figure 5B:
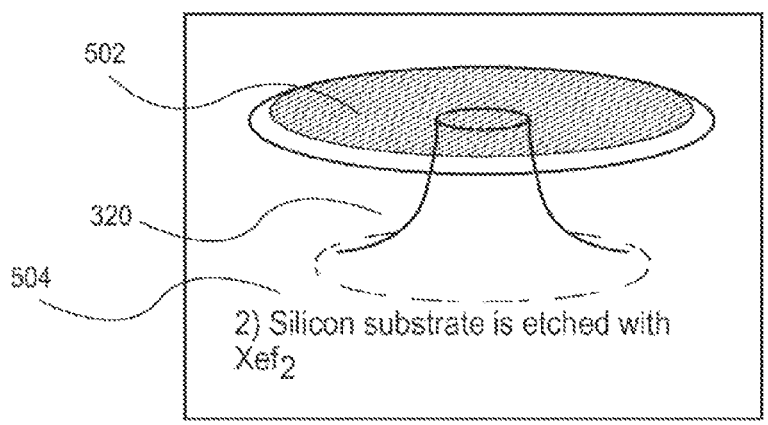
Figure 5C:
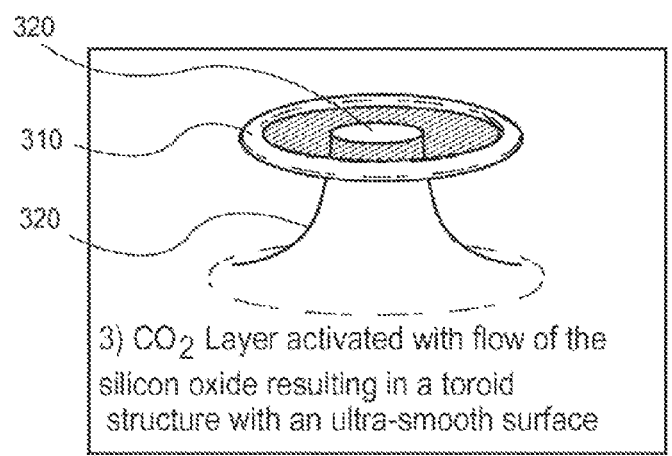

Referring to FIG. 4 and with further reference to FIGS. 5A-C, one method 400 of fabricating a toroid-shaped micro-cavity 310 supported by a substrate 320 as shown in FIG. 3 includes wet etching a photolithography patterned silica or silicon dioxide ($SiO_2$) disk or circular pad 502 on a silicon substrate 504 or other suitable substrate (FIG. 5A) in step 402. This may be done using a hydrogen fluoride (HF) solution or other suitable etchant. In step 404, the silica disk 502 is exposed to a second etchant such as xenon difluoride ($XeF_2$) gas. $XeF_2$ is an etchant with high selectivity that is currently utilized to produce, for example, Micro-Electrical Mechanical Systems (MEMS) devices. The $XeF_2$ gas removes or etches portions of the silicon base beneath the periphery of the silica disk 502 (FIG. 5B), thereby forming the tapered silicon support 320 (as shown in FIG. 3). In step 406, a laser, such as an Eximer or $CO_2$ laser, is applied to the undercut periphery of the silica disk 502 (FIG. 5C). As a result, the periphery portions of the silica disk 502 are melted or partially or completely liquefied to reflow and form a toroid-shaped micro-cavity 310 having ultra smooth surfaces (FIGS. 3 and 5C). Further aspects of toroid-shaped micro-cavities 310 and methods of fabrication are described in further detail in U.S. application Ser. No. 10/678,354/Publication No. 2004/0179573 A1, and U.S. application Ser. No. 11/733,480/Publication No. 2007/0269901, the contents of which were previously incorporated herein by reference as though set forth in full.

Figure 6A:
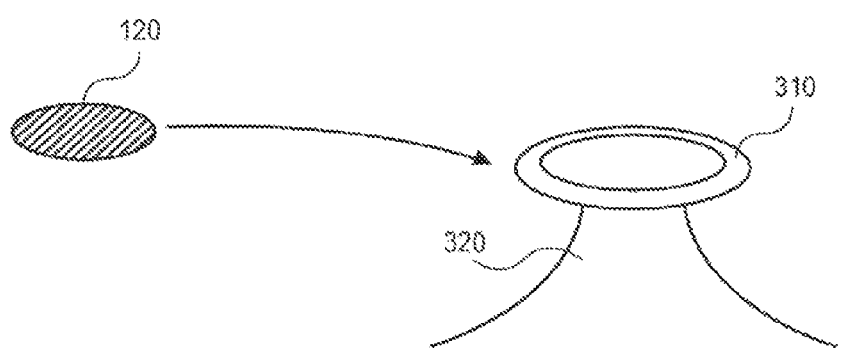
FIG. 6A illustrates application of a deformable coating to a toroid-shaped micro-cavity.
Figure 6B:
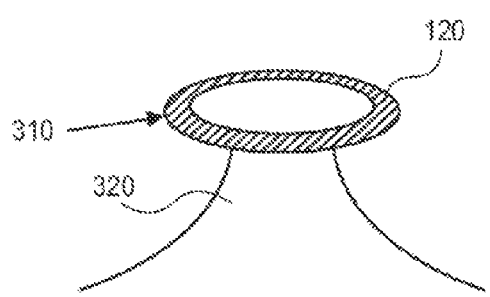
FIG. 6B illustrates a gas or vapor sensor constructed according to one embodiment having a toroid-shaped micro-cavity and a coating that deforms in the presence of a target gas or vapor.

Referring to FIGS. 6A-B, a deformable coating 120 is applied to at least a portion of the toroid-shaped micro-cavity 310. According to one embodiment, the coating 120 is applied to cover the toroid-shaped micro-cavity 310, as generally illustrated in FIG. 6B. The coating 120 can be applied to the toroid-shaped micro-cavity 310 and other micro-cavities using various known techniques including, for example, spin coating, evaporation, and growth nucleation.

Figure 7:
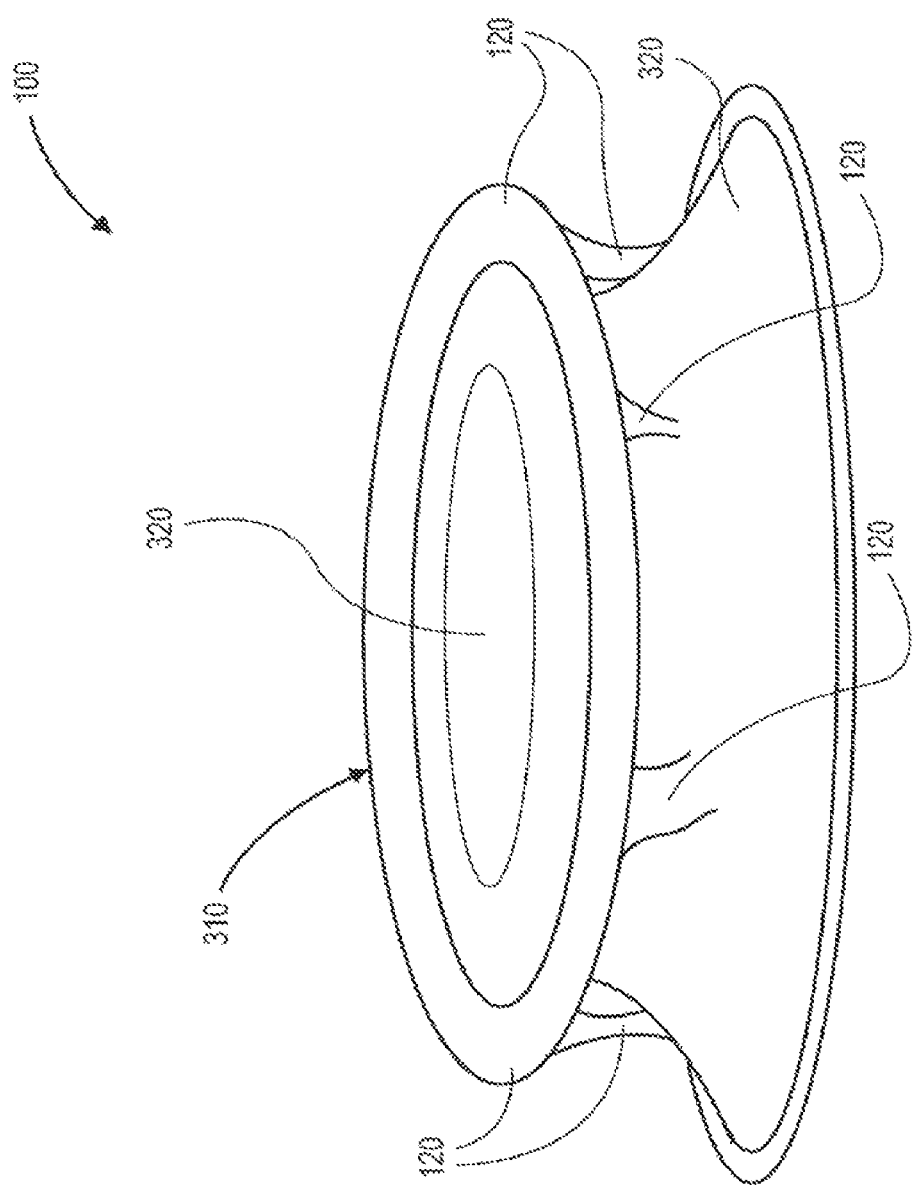
FIG. 7 is a perspective view of a gas or vapor sensor constructed according to one embodiment in the form of a toroid-shaped micro-cavity having a deformable coating.

FIG. 7 is a scanning electron micro-graph of a gas or vapor sensor constructed according one embodiment that comprises a toroid-shaped micro-cavity 310 fabricated using the method illustrated in FIGS. 4 and 5A-C. In the illustrated embodiment, the toroid-shaped micro-cavity 310 is a silica micro-cavity that is coated or covered with a PMMA coating 120 using known spin coating techniques. For this purpose, coatings 120 may be applied using, for example, spin speeds ranging from about 2500 to about 7000 rpm for corresponding times of about 75 to about 25 seconds. As shown in FIG. 7, the deformable coating 120 covers the entire toroid-shaped micro-cavity 310, and portions of the coating 310 extend between a bottom surface of the toroid-shaped micro-cavity 310 to a tapered portion of the substrate 320 as a result of the spin-coating process. In this particular embodiment, the outer diameter of the toroid-shaped micro-cavity 310 is about 80 micrometers, and the thickness of the PMMA coating 120 is about 1 micrometer.

Figure 8A:
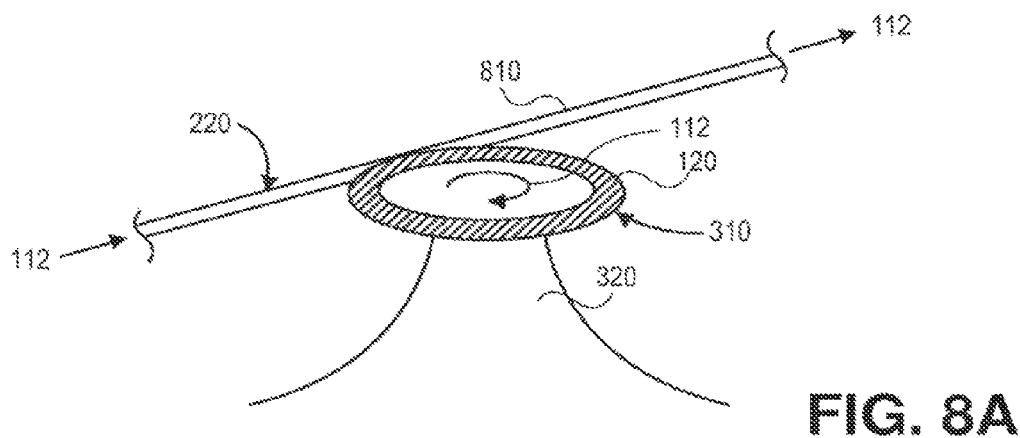
FIG. 8A is a perspective view of gas or vapor sensor in the form of a toroid-shaped micro-cavity having a deformable coating that is optically coupled to waveguide for coupling optical energy into the micro-cavity.
Figure 8B:
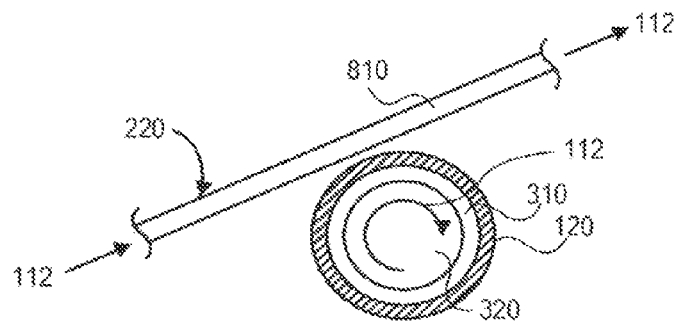
FIG. 8B is a top view of a gas or vapor sensor in the form of a toroid-shaped micro-cavity having a deformable coating that is optically coupled to the waveguide.

Referring to FIGS. 8A-B, a gas or vapor sensor 100 constructed according to one embodiment and having a coated toroid-shaped micro-cavity 310 may be coupled to a coupler or waveguide 220, e.g., in the form of a fiber 810. The fiber 810 is coupled to a light source or laser 210, and light or optical energy 112 is coupled into the coated toroid-shaped micro-cavity 310 using the fiber 810. One example of fiber 810 that may be used for this purpose is a fiber taper or coupler 900, as generally illustrated in FIG. 9.

Figure 9:
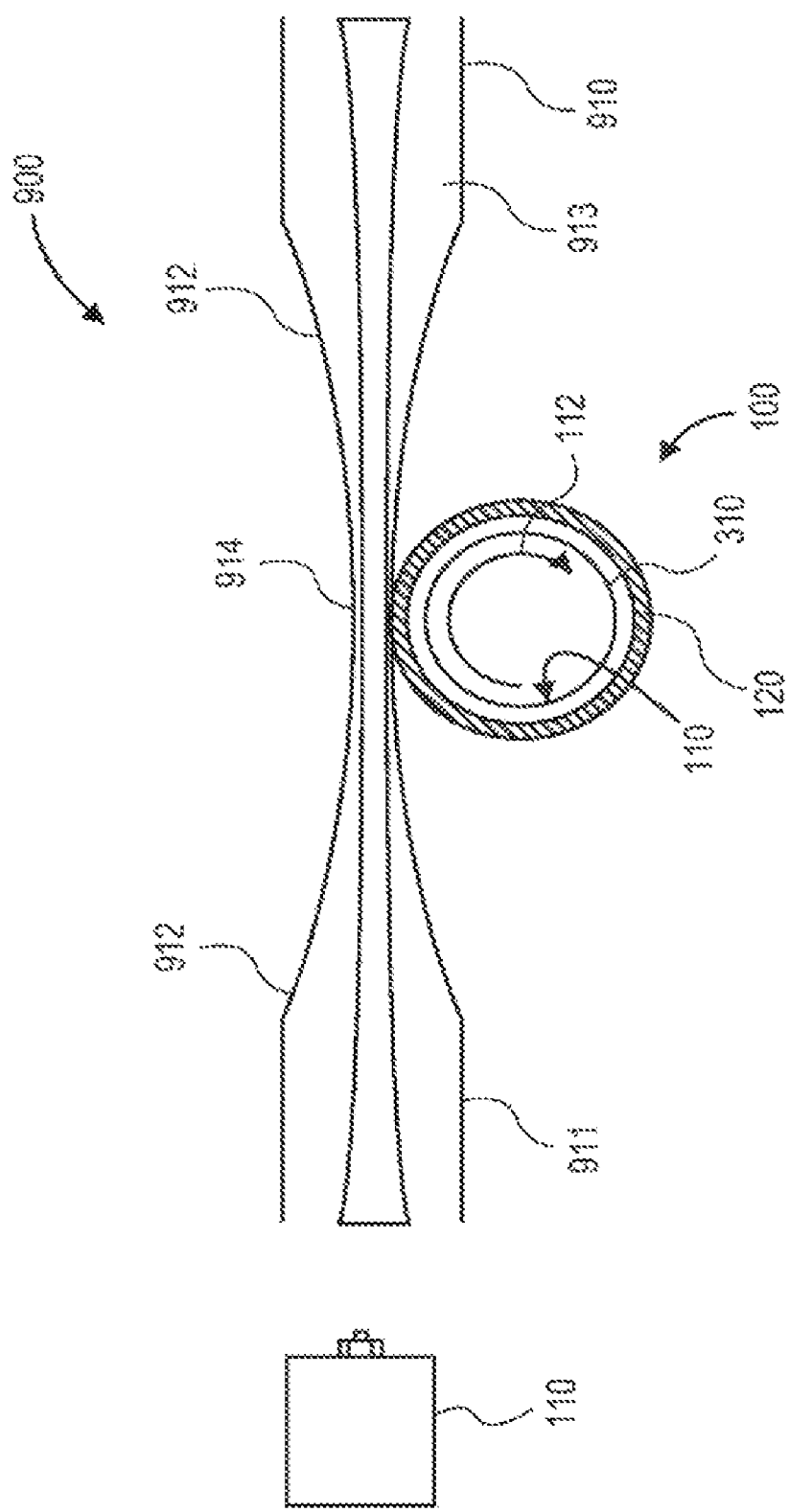
FIG. 9 illustrates one example of a coupler or waveguide in the form of a fiber taper coupler that may be utilized with embodiments.

Referring to FIG. 9, in one known fiber taper or coupler 900, a transmission media 910 carries optical energy 112 that is to resonate or circulate within a micro-cavity 110 such as a toroid-shaped micro-cavity 310. Active media that are excited by optical pumps can also be associated with the toroid-shaped micro-cavity 310 to facilitate the lasing of a signal within a frequency band of interest. In one embodiment, the transmission media 910 is a fiber waveguide, e.g., a tapered waveguide as shown in FIG. 9, although other waveguide configurations can also be utilized. Tapered sections 912 and the intermediate waist region 914 of the waveguide 910 may be provided, as is known, by stretching a fiber (e.g., a single mode fiber) under controllable tension as it is softened by one or more fixed or movable heat sources (e.g., torches). The diameter of the tapered waist region 914 may be several micrometers, e.g., about 2 micrometers. The toroid-shaped micro-cavity 310, which may be an ultra-high Q micro-cavity, is coupled to the waist region 914 of the fiber 910. The diameter of the waist region 914 can be adjusted to properly phase-match to the toroid-shaped micro-cavity 310.

A light source or optical pump 110 such as a laser is optically connected to a first end 911 of the fiber 910. The optical pump 110 transmits a signal or optical energy 112 along the fiber 910 through the fiber taper 912 and the waist region 914 where it is coupled into the toroid-shaped micro-cavity 310. Evanescent optical energy 112 that emanates from the waist region 914 is coupled into the toroid-shaped micro-cavity 310 such that one or more excited laser signals circulate or resonate within the toroid-shaped micro-cavity 310 with effectively total internal reflection and with minimal internal attenuation and radiative losses, e.g., in a Whispering Gallery Mode (WGM) or other resonant mode. A portion of the resonant optical energy 112 evanesces beyond the micro-cavity 310/coating 120 and is presented for coupling back into the waveguide waist 406, through an outgoing tapered region 912 and into the outgoing end 913 of the fiber 910. Further aspects of a suitable coupler 900 for use in embodiments are described in U.S. Pat. No. 6,741,628 to Painter et al., the contents of which are incorporated herein by reference.

Figure 10:
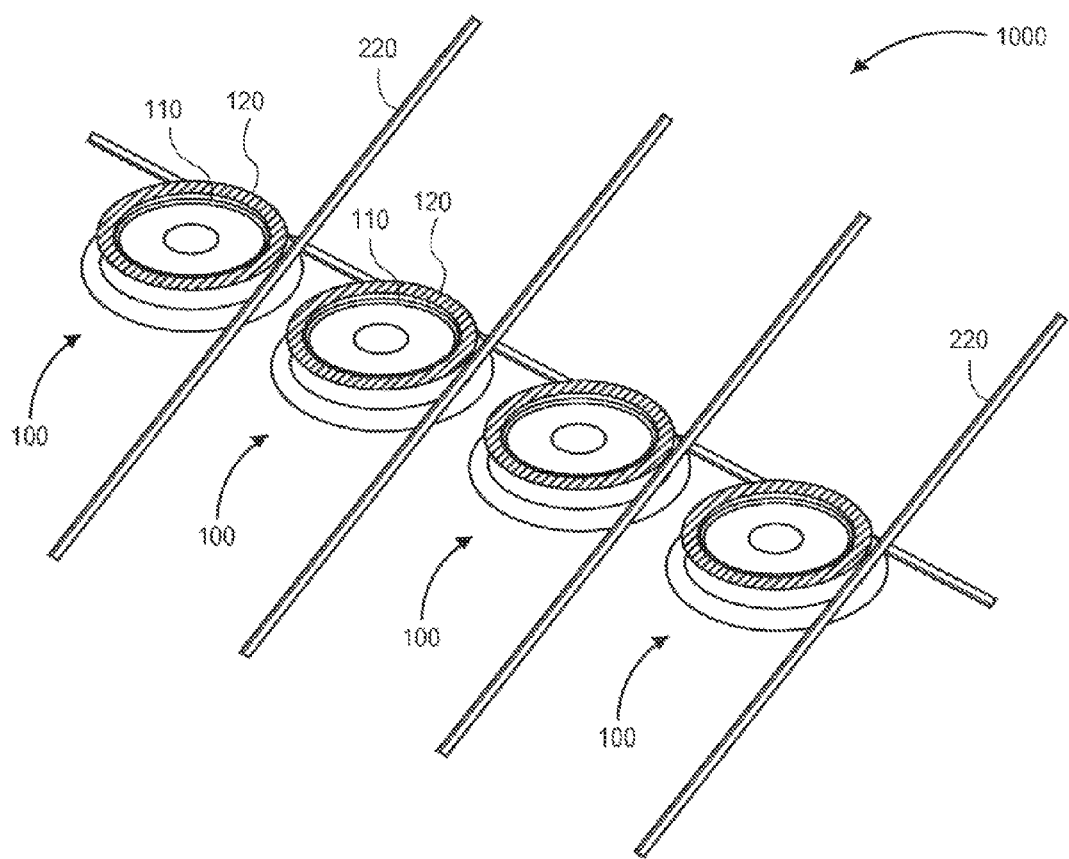
FIG. 10 illustrates an array of gas vapor sensors in the form of toroid-shaped micro-cavities having deformable coatings and that are coupled to waveguides.

Referring to FIG. 10, although various figures illustrate a single gas or vapor sensor 100 including a toroid-shaped micro-cavity 310 and a deformable coating 120 and associated coupler 220, e.g., a taper fiber coupler 900, other embodiments are directed to an array 1000 of gas or vapor sensors 100 that are coupled to one or more or respective couplers or waveguides 220. An array 1000 of gas or vapor sensors 100 may have coated micro-cavities 110 of the same or different shapes and/or sizes, which is useful since sensors 100 having micro-cavities 110 of different sizes have different resonant wavelengths to allow for high throughput detection of multiple gases or vapors. Further, different resonant wavelength characteristics may be achieved based on other characteristics such as the shape and/or material of the micro-cavity 110. Micro-cavities 110 of an array 1000 of sensors 100 may be made of the same material or different materials and may include the same coating 120 or different coatings 120. A random array of micro-cavities 110 may also be formed and characterized after fabrication. For ease of explanation and illustration, reference is made to an individual sensor 100, but embodiments may include arrays 1000 of various numbers of sensors 100 that can be structured in different manners.

Figure 11A:
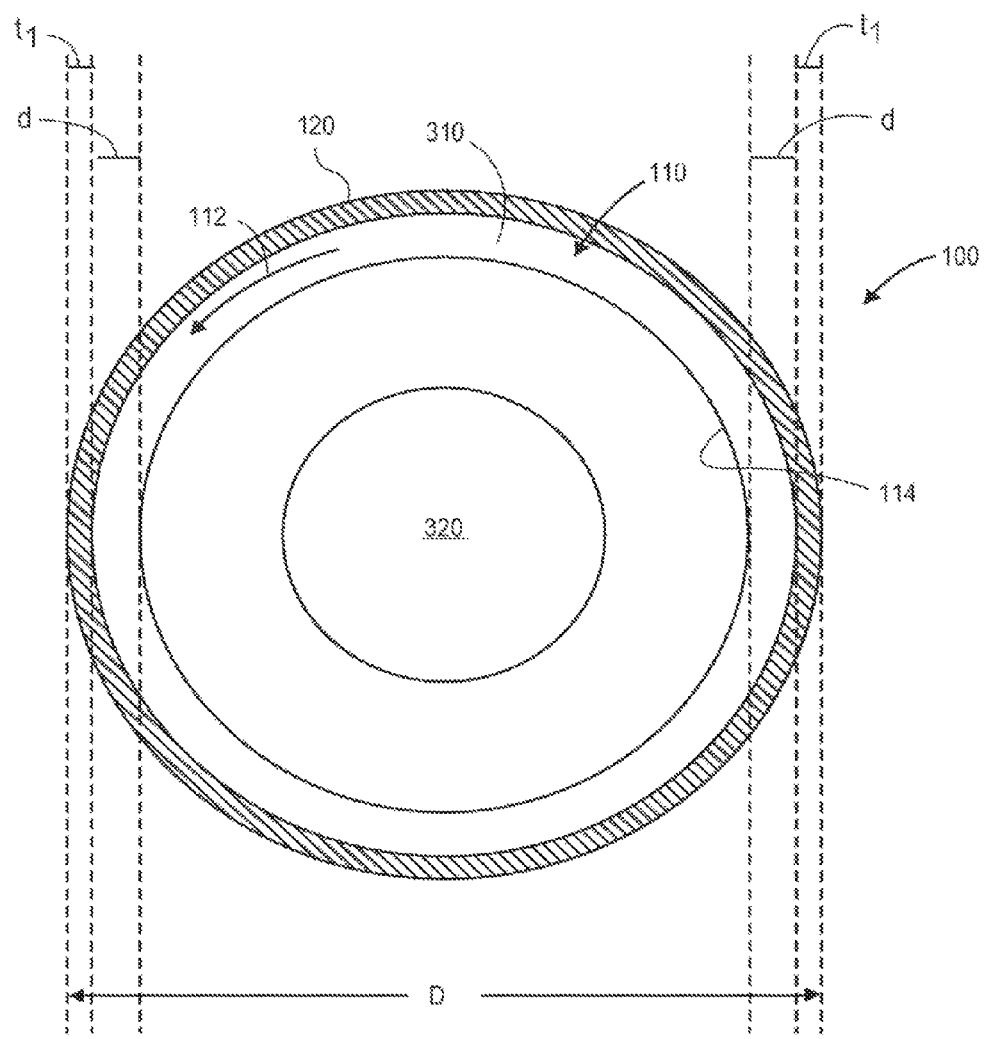

FIGS. 11A-D illustrate in further detail one embodiment of a gas or vapor sensor 100 including a deformable coating 120 that is applied to an outer surface of a toroid-shaped micro-cavity 310 and how deformation of the coating 120 may be utilized to detect the presence of a gas or vapor 130. Referring to FIG. 11A, a toroid-shaped micro-cavity 310 is illustrated as being supported by a substrate 320 and having a deformable coating 120 such as a polymer coating applied thereto. The substrate 320 forms a support pillar such that the inner edge 114 of the micro-cavity 110 extends around an outer edge of the top surface of the substrate 120. Thus, the substrate 120 effectively supports and elevates the micro-cavity 110 above a bottom surface of the substrate 320.

An outer or major diameter D1 of the sensor 100 is defined by the outer edges of the coating 120, and an inner diameter D2 is defined between opposite inner edges 114 of the toroid-shaped micro-cavity 310. The toroid-shaped micro-cavity 310 has a width or diameter (d), and the coating 120 applied thereto has a first or initial thickness (t1). As one example, for a silica toroid-shaped micro-cavity 310, the major diameter D may be about 30 micrometers to about 2000 micrometers, the width or diameter (d) of the micro-cavity 310 may, for example, be about 20 micrometers to slightly smaller than the major diameter, e.g., about 22 micrometers to about 1998 micrometers, and the initial thickness (t1) of the deformable coating 120 may be about 10 nanometers to about 2 micrometers. It should be understood that FIG. 11A and other figures are not necessarily to scale.

Figure 11D:
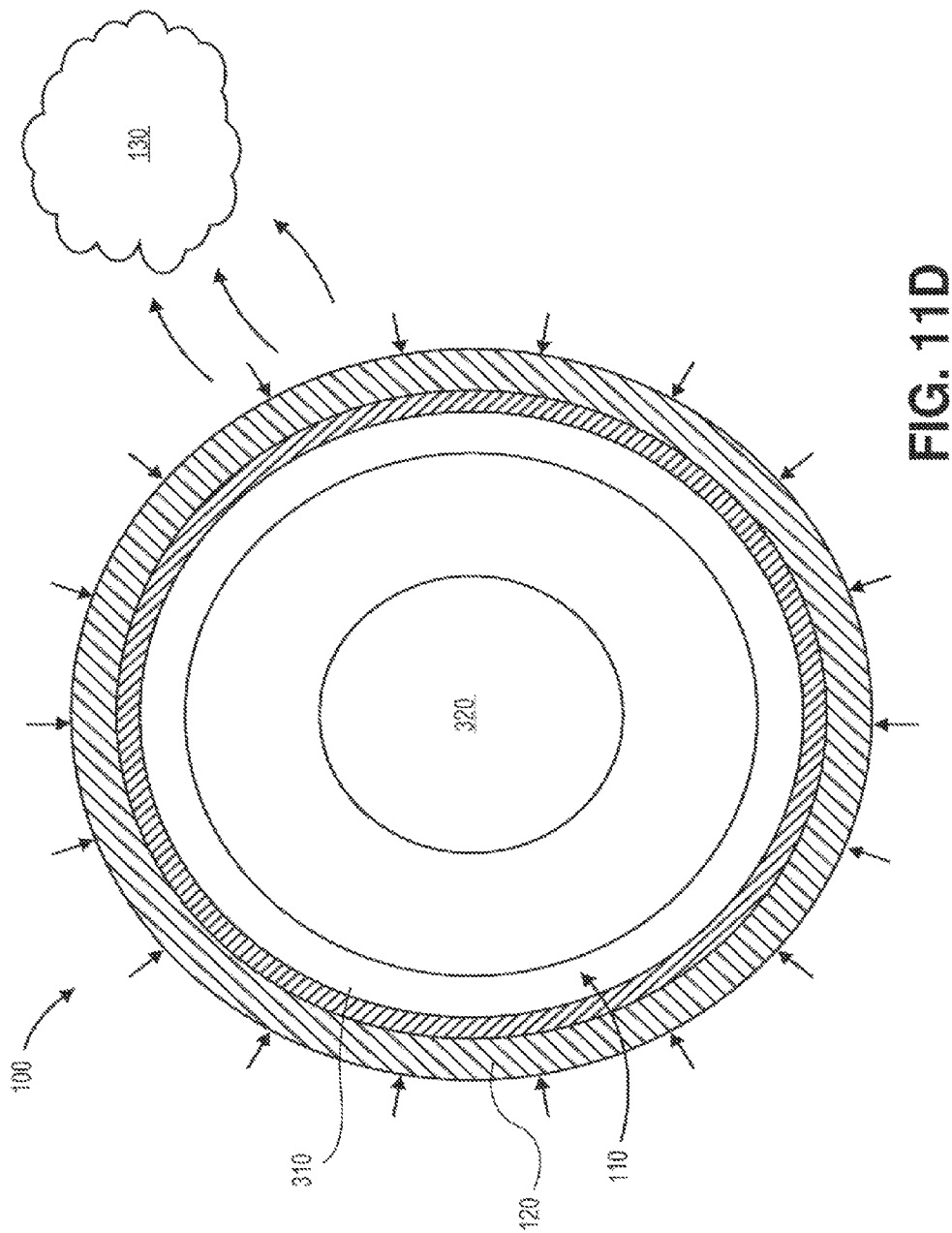

Referring to FIG. 11B, the sensor 100 is exposed to or placed within a gas or vapor environment 130. As a result, referring to FIG. 11C, the deformable polymer coating 120 expands or swells, e.g., by about 1 to about 50% to a second thickness (t2) such that the optical energy 112 resonates within the micro-cavity 310 and/or the enlarged coating 120. It should be understood that FIG. 11C may not accurately depict the magnitude of swelling or relative dimensions of the toroid-shaped micro-cavity 310 and the coating 120, but the swelling or expansion of the coating 120 is shown in FIG. 11C for purposes of illustration. Referring to FIG. 11D, the gas or vapor 130 may then diffuse out of the coating 120, thus causing the coating 120 to shrink or contract, e.g., to its original thickness (t1) (FIG. 11A), if the coating 120 provides for deformation reversibility.

Figure 12:
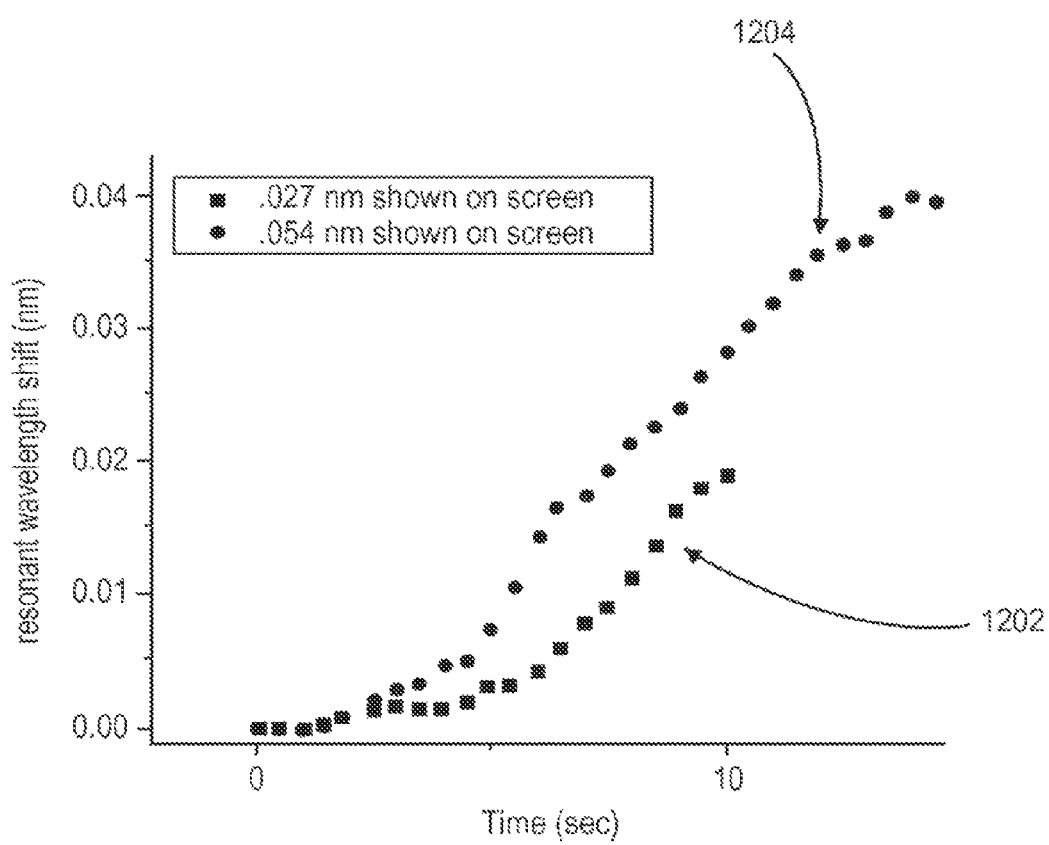
FIG. 12 is a graph illustrating test results of embodiments of a gas or vapor sensor including a toroid-shaped micro-cavity having a polymer coating and illustrating the swelling response of the polymer coating relative to resonant wavelength shift as a result of absorbing acetone.

FIG. 12 is a graph summarizing results of a test that was performed to demonstrate how gas or vapor sensor 100 embodiments perform. The test involved coupling or placing a sensor 100 having an ultra-high Q toroid-shaped micro-cavity 310 (e.g., as shown in FIG. 3) fabricated and spin coated with a PMMA coating or film 120 as described with reference to FIGS. 4-8B. The sensor 100 was placed in an air environment, and optical energy 112 was coupled into the toroid-shaped micro-cavity 310/PMMA coating 120. Initial resonance data was recorded, and then the sensor 100 was exposed to a small quantity of acetone. During the next few seconds, the acetone was absorbed by the PMMA coating 120, thereby causing the PNMA coating 120 to expand or swell (as generally illustrated in FIG. 11C). This swelling resulted in a red-shift of the resonant wavelength of the optical energy 112 resonating within the micro-cavity 310/coating 120. The acetone eventually evaporated and diffused out of the PMMA coating 120, thereby resulting in contraction of the PMMA coating 120 (as generally illustrated in FIG. 11D) and a blue-shift of the resonant wavelength of the optical energy 112.

The graph illustrated in FIG. 12 includes two sets of data illustrating how the resonant wavelength (nm) of optical energy 112 changed over time (seconds) as the PMMA coating 120 absorbed the acetone. The first data set 1202 illustrates test results using a laser scanning range of 0.27 nm. Thus, this data set 1202 illustrates a resonant wavelength shift of about 0.02 nm over 10 seconds as the PMMA coating 120 absorbed the acetone, thereby causing the coating 120 to expand or swell, which resulted in the resonant wavelength shift. The second set of data 1204 illustrates test results using a laser scanning range of 0.54 nanometer to capture a larger range of the swelling response of the PMMA coating 120 and illustrates a resonant wavelength shift of about 0.04 nanometer over 15 seconds. Thus, the test involving acetone and a PMMA coating 120 applied to a toroid-shaped micro-cavity 310 demonstrated that coating 120 deformation can be used to detect gas or vapors 130 based on a resonant wavelength shift, and that embodiments may be adapted for rapid and reversible responses using the same toroid-shaped micro-cavity 310.

Although gas or vapor sensor 100 embodiments and applications thereof are described with reference to a toroid-shaped micro-cavity 310, embodiments may also be implemented using micro-cavities 110 of other shapes, sizes, and materials. For example, referring to FIG. 13, a gas or vapor sensor 100 constructed according to another embodiment comprises a spherical micro-cavity 1300 having a deformable coating 120 such as a polymer, one example of which is PMMA. One example of a micro-sphere 1300 that may be utilized in embodiments is described in U.S. Pat. No. 6,741, 628, the contents of which were previously incorporated herein by reference.

One manner of fabricating a micro-sphere 1300 for use in embodiments involves melting a small piece of glass material, e.g., phosphate glass, in a crucible. While the phosphate is molten, the tip of a silica fiber taper, which has a higher melting point, is placed into the melt. As the silica "stem" is extracted, a small phosphate taper is formed on the end of the silica taper. A laser is used to melt the end of the phosphate taper, forming a sphere under surface tension. The silica fiber stem is finally placed in a fiber chuck and used as a handling rod to control and position the phosphate sphere.

Figure 13:
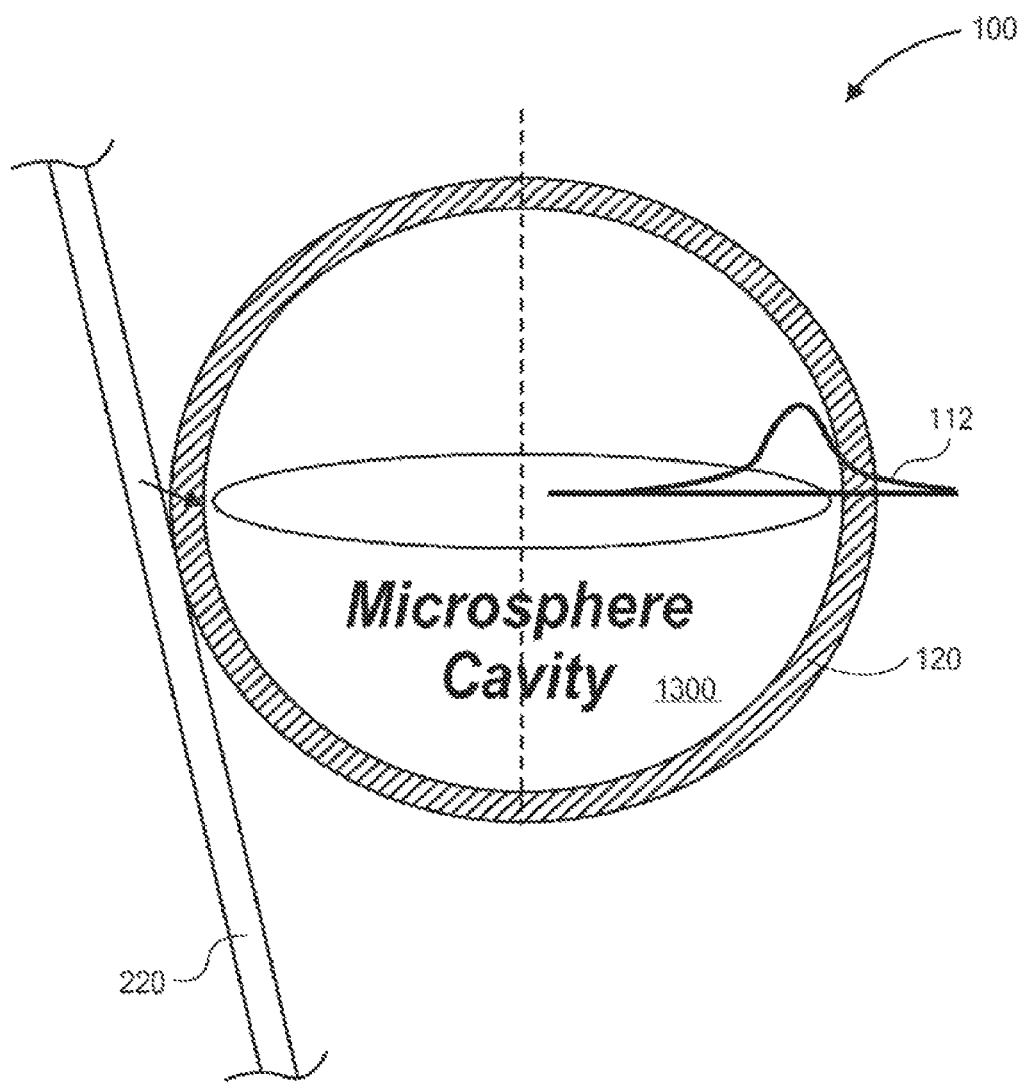
FIG. 13 illustrates a gas or vapor sensor constructed according to another embodiment that includes spherical micro-cavity or micro-sphere and a deformable coating or film.

As shown in FIG. 13, a gas or vapor sensor 100 constructed according to one embodiment is formed by applying a deformable coating or film 120, such as a polymer coating, to the outer surface of the micro-sphere 1300 or a portion thereof using known techniques such as spin coating, evaporation, growth nucleation and dip-coating. The micro-sphere 1300 may be made of silica and other suitable materials, and may have a diameter of about 100 micrometers to about 3 millimeters, e.g., about 1 millimeter. The coating 120 applied to the micro-sphere 1300 may be a polymer coating such as PMMA and have a thickness of about 1 micrometer. Other micro-sphere 1300 and coating 120 materials and dimensions and thicknesses may be utilized, e.g., as discussed above with respect to the toroid-shaped micro-cavity 310.

A coupler or waveguide 220 can be positioned to couple optical energy 112 into the micro-sphere 1300. Optical energy 112 resonates within the micro-sphere 1300, e.g. in a WGM or other resonant mode. For example, optical energy 112 may be coupled into the micro-sphere 1300 through a planar waveguide or utilizing total internal reflection fluorescence (TIRF). Other evanescent coupling devices and techniques to interrogate the micro-spheres 1300 involve the use of tapered fibers (e.g., as illustrated in FIG. 9) and/or prism waveguides.

The coupler or waveguide 220 is positioned such that optical energy 112 can be coupled into and resonate within the coated micro-sphere 1300 depending on the wavelength of the optical energy 112. The wavelength of optical energy 112 is slowly varied and one or more resonant wavelengths of a micro-sphere 1300 are reached. As a result, light 112 at these resonant wavelengths will couple into the micro-sphere 1300 and continuously circulate or resonate within the micro-sphere 1300/coating 120, causing the micro-sphere 1300 to light up.

Figure 14:
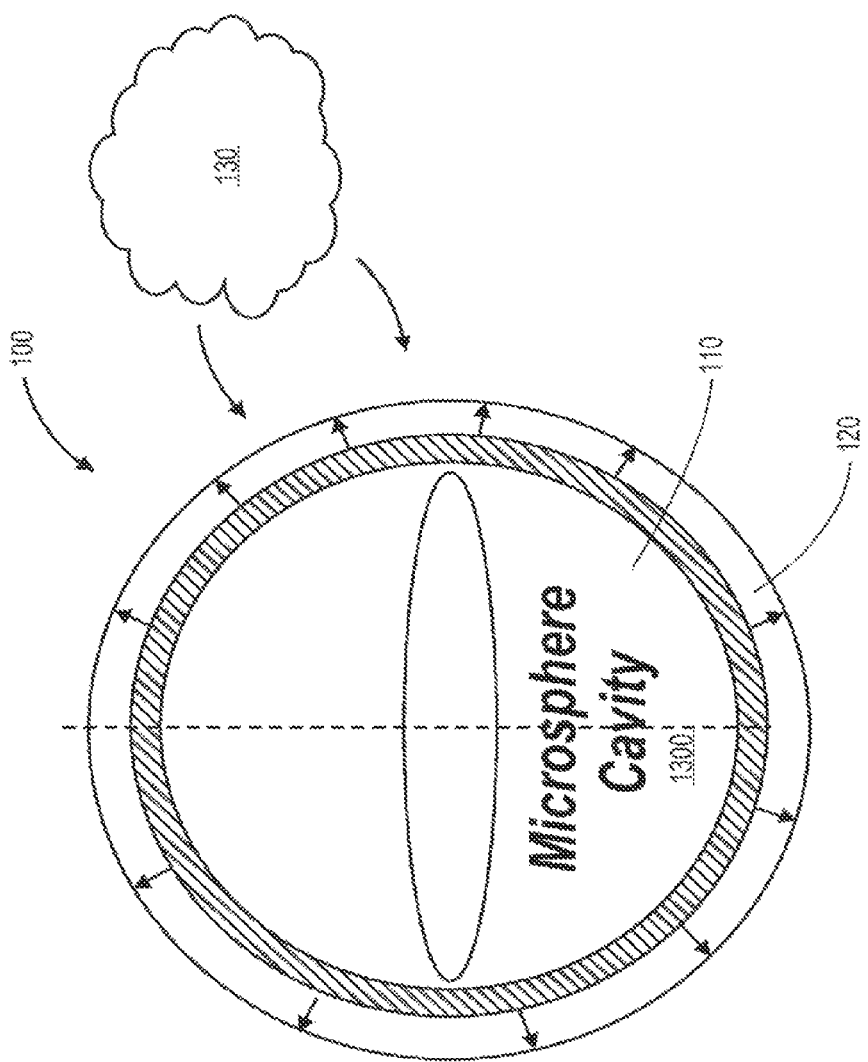
FIG. 14 illustrates how the coating on the micro-sphere as shown in FIG. 13 expands or swells as a result of absorbing a gas or vapor.

As shown in FIG. 14, when the gas or vapor sensor 100 in the form of a coated micro-sphere 1300 is exposed to or placed within a gas or vapor environment 130, the coating 120 expands or swells, e.g., by about 1% to about 50%, to a second thickness, e.g., about 1.01 micrometer to about 1.5 micrometer. As a result, optical energy 112 resonates within the micro-cavity 310 and/or the enlarged or swelled coating 120, thereby resulting in a shift of the resonant wavelength or red shift of the optical energy 112. In certain embodiments, this process may be reversible such that when the gas or vapor 130 diffuses out of the coating 120, the coating 120 contracts or shrinks, resulting in a shift or blue shift of the resonant wavelength.

In certain embodiments, an array of gas or vapor sensors 100 having coated micro-spheres 1300 may be utilized. An array of such sensors 100 may have coated micro-spheres 1300 of the same or different sizes, which is useful since an array of sensors 100 having micro-spheres 1300 of different sizes has different resonant wavelengths to allow for high throughput detection of multiple gases or vapors. Further, micro-spheres 1300 of an array may be made of the same material or different materials, and may include the same coating 120 or different coatings 120. A visual spatial-temporal pattern is generated as different micro-resonators of the array light up at different resonant wavelengths.

Embodiments of gas or vapor sensors 100 can be implemented using micro-cavities 110 having other shapes besides toroid and spherical shapes as described with reference to FIGS. 1-14. For example, gas or vapor sensors 100 constructed according to other embodiments may include micro-cavities 110 in the form of micro-disks, micro-pillars and micro-rings, and each of these micro-cavities 110 may be coated with a deformable coating 120 that can change shape and/or size as a result of absorbing a gas or vapor 130. Further, an array of such coated micro-cavities may also be fabricated.

Further, the Q value and sensitivity of sensor 100 embodiments having a coated micro-cavity 110 can vary and can be configured to detect trace amounts of airborne particulates and gases. For example in certain embodiments, a gas or vapor sensor 100 constructed according to one embodiment having a toroid-shaped micro-cavity 310 has an ultra-high Q value of greater than $10^6$, e.g., $10^7$ and greater than $10^8$. Spherical micro-cavities 1300 may have similar Q values.

Additionally, embodiments can be used to detect various types of gases or vapors 130. For example, it should also be understood that although this specification describes examples involving detection of acetone to demonstrate the effectiveness of embodiments, embodiments can be applied to various other monitoring and detection applications and detection of other gases and vapors 130. According to one embodiment, $NO_2$ is detected using a polyethyleneimine coating 120. According to another embodiment, $NH_3$ is detected using a Nafion® coating 120. According to a further embodiment, chlorinated hydrocarbons, aromatic hydrocarbons, aliphatic hydrocarbons, acetate and alcohols are detected using a Flurosiloxane coating 120. In another embodiment, 1,2-dichloro ethane, bromochloromethane, trichloromethane, dichloromethane and tetrachloromethane are detected using a poly(p-xylylene) coating 120. Sensor 100 embodiments may be utilized to detect other gases, vapors and airborne particulates of interest using the same or different coatings 120 and may be used in various applications including, for example, environmental monitoring, chemical detection, explosives detection, toxicology, medical diagnostics and other applications and embodiments may be integrated into gas sampling and concentration systems. For example, sensor 100 embodiments may be utilized in cryogenic, sorbent trapping, polyurethane foam, activated carbon, molecular sieve and semi-permeable membrane sampling and concentration systems.

Although references have been made in the foregoing description to various embodiments, persons of ordinary skill in the art will recognize that insubstantial modifications, alterations, and substitutions can be made to the described embodiments without departing from the invention as recited in the accompanying claims. For example, embodiments of resonant gas or vapor sensors can be made of various resonator materials and may have various shapes, sizes and coatings. Further, arrays of sensors may have various numbers of sensors, which may have the same or different micro-cavities and deformable coatings. Further, various types and thicknesses of deformable coatings may be utilized.

What is claimed is:

1. A sensor for detecting a gas or vapor, the sensor comprising:
    a resonant micro-cavity;
    a deformable coating on an outer surface of the resonant micro-cavity, wherein material properties of the deformable coating are such that the coating expands and a dimension of the deformable coating changes due to absorption of the gas or vapor, and the expansion causes a red shift of the wavelength of optical energy resonating within the micro-cavity, the resonant micro-cavity and the deformable coating being configured for detection of the gas or vapor based at least in part upon the change of the dimension of the deformable coating.

2. The sensor of claim 1, wherein the material properties of the coating are such that the coating expansion and the red shift are reversible as the gas or vapor diffuses out of the coating.

3. The sensor of claim 1, wherein the resonant micro-cavity has a Q factor greater than $10^6$ and is a planar micro-cavity.

4. A sensor for detecting a gas or vapor, the sensor comprising:
    a resonant micro-cavity;
    a deformable polymer coating on an outer surface of the resonant micro-cavity, wherein material properties of the polymer coating are such that the polymer coating expands and a dimension of the deformable polymer coating changes due to absorption of the gas or vapor, and the expansion causes a red shift of the wavelength of optical energy resonating within the micro-cavity shift of the wavelength of optical energy resonating within the micro-cavity, the resonant micro-cavity and the deformable polymer coating being configured for detection of the gas or vapor based at least in part upon the change of the dimension of the deformable polymer coating.

5. The sensor of claim 4, wherein the material properties of the coating are such that the polymer coating expansion and the red shift are reversible as the gas or vapor diffuses out of the polymer coating.

6. The sensor of claim 4, wherein the resonant micro-cavity is a spherical or spheroid micro-cavity.

7. The sensor of claim 4, wherein the resonant micro-cavity is a planar micro-cavity.

8. The sensor of claim 7, wherein the resonant micro-cavity is a toroid-shaped micro-cavity.

9. The sensor of claim 4, wherein the polymer coating is polymethyl methacrylate (PMMA), polyethyleneimine, fluorosiloxane or polyp-xylylene).

10. The sensor of claim 4, wherein the polymer coating is configured to detect $NO_2$, $NH_3$, a chlorinated hydrocarbon, an aromatic hydrocarbon, an aliphatic hydrocarbon, an acetate, an alcohol, 1,2-dichloroethane, bromochloromethane, trichloromethane, dichloromethane or tetrachloromethane.

11. The sensor of claim 4, wherein the resonant micro-cavity is an ultra-high Q resonant micro-cavity.

12. The sensor of claim 11, wherein the material properties of the polymer coating are such that the coating expansion and the red shift are reversible as the gas or vapor diffuses out of the polymer coating.

13. The sensor of claim 11, wherein the resonant micro-cavity has a Q factor greater than $10^6$.

14. The sensor of claim 4, further comprising:
a substrate supporting the resonant micro-cavity, wherein an outer edge of the resonant micro-cavity extends outwardly beyond a top of the substrate.

15. The sensor of claim 1, wherein the resonant micro-cavity is a spherical or spheroid micro-cavity.

16. The sensor of claim 1, wherein the resonant micro-cavity is a planar, toroid-shaped micro-cavity.

17. The sensor of claim 1, wherein the resonant micro-cavity and the deformable coating are configured for detection of an unlabeled gas or vapor molecule.

18. The sensor of claim 4, wherein the resonant micro-cavity and the deformable polymer coating are configured for detection of an unlabeled gas or vapor molecule.

19. The sensor of claim 1, further comprising:
a substrate supporting the resonant micro-cavity, wherein an outer edge of the resonant micro-cavity extends outwardly beyond a top of the substrate.

20. The sensor of claim 1, wherein the resonant micro-cavity is a planar, toroid-shaped resonant micro-cavity.

21. The sensor of claim 20, further comprising:
a substrate supporting the planar, toroid-shaped resonant micro-cavity, wherein an outer edge of the toroid-shaped resonant micro-cavity extends outwardly beyond a top of the substrate.

22. The sensor of claim 16, further comprising:
a substrate supporting the planar, toroid-shaped resonant micro-cavity, wherein an outer edge of the toroid-shaped resonant micro-cavity extends outwardly beyond a top of the substrate.

* * * * *